US007674768B2

(12) United States Patent
Ho et al.

(10) Patent No.: US 7,674,768 B2
(45) Date of Patent: Mar. 9, 2010

(54) PROCESSES FOR PREPARING EPTIFIBATIDE

(75) Inventors: Guojie Ho, Sudbury, MA (US); Antoinette D. Paone, Lexington, MA (US); Luciano Forni, La Louviere (BE); Catherine De Tollenaere, Louvain-la-Neuve (BE); Brice Bonnet, Levallois-Perret (FR); Christine Devijver, Brussels (BE)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 423 days.

(21) Appl. No.: 11/101,983

(22) Filed: Apr. 8, 2005

(65) Prior Publication Data

US 2006/0036071 A1 Feb. 16, 2006

Related U.S. Application Data

(60) Provisional application No. 60/560,453, filed on Apr. 8, 2004.

(51) Int. Cl.
*A61K 38/00* (2006.01)
*C07K 16/00* (2006.01)

(52) U.S. Cl. .......................................... 514/9; 530/333
(58) Field of Classification Search ........................ None
See application file for complete search history.

(56) References Cited

U.S. PATENT DOCUMENTS

| 4,954,616 | A |  | 9/1990 | Callens et al. ............... 530/333 |
| 5,318,899 | A |  | 6/1994 | Scarborough et al. ...... 435/69.6 |
| 5,506,362 | A |  | 4/1996 | Callens et al. ............... 548/497 |
| 5,686,570 | A |  | 11/1997 | Scarborough et al. ....... 530/330 |
| 5,747,447 | A |  | 5/1998 | Swift et al. ...................... 514/9 |
| 5,837,218 | A | * | 11/1998 | Peers et al. .................. 424/1.69 |
| 2004/0249121 | A1 | * | 12/2004 | Tovi et al. .................... 530/307 |

FOREIGN PATENT DOCUMENTS

WO          03/093302 A2    11/2003

WO          WO/2007009946   1/2007

OTHER PUBLICATIONS

Zhao, et al, "Stabalization of eptifibatide by cosolvents," Int. Journal of Pharmaceuticals, 218 (2001) 43-56.*
Snyder, et al, Practical HPLC Development, 2nd Edition, pp. 497 and 498.*
Simmonds, R.G., et al, "Synthesis of disulfide-bridged fragments of omega-conotoxins GVIA and MVIIA. Use of Npys as a protecting/activating group for cysteine in Fmoc syntheses," Int J Pept Protein Res. Apr. 1994;43(4):363-6.*
Thornber C.W. Isosterism and Molecular Modification in Drug Design, Chem Soc. Rev. (1979) vol. 8(4), pp. 563-580.*
R. Callens, "Peptisyntha's Method of Producing GMP Peptides on an Industrial Scale" presented at IBC's $2^{nd}$ International Conference on Peptide Technologies, San Diego, 1999.
Millennium Pharmaceuticals Inc.: "Integrilin (eptifibatide) injection," Internet Article, Apr. 2004, Retrieved from the Internet: www.fda.gov/medwatch/safety/2004/jul_PI_Integrilin_PI.pdf, retrieved on Nov. 8, 2004.
Scarborough, R. M. et al., "Design of Potent and Specific Integrin Antagonists," *J Biol Chem*, Jan. 15, 1993, 268(2): 1066-1073.
Database CA Online, Chemical Abstracts Service, Columbus, Ohio, US; vol. 116, abstract No. 248916, 1992 XP002304466 & *Journal of Chromatography*, vol. 597, No. 1-2, 1992, pp. 425-428.

* cited by examiner

*Primary Examiner*—Cecilia Tsang
*Assistant Examiner*—Thomas S Heard
(74) *Attorney, Agent, or Firm*—Honigman Miller Schwartz and Cohn LLP; Thomas A. Wootton; Noel E. Day

(57) ABSTRACT

The present invention provides, inter alia, convergent processes for preparing eptifibatide that involve coupling a 2-6 eptifibatide fragment to an activated cysteinamide residue to form a 2-7 eptifibatide fragment, attaching a mercaptopropionic acid residue to the 2-7 eptifibatide fragment through disulfide bond formation, coupling the peptide intramolecularly, and removing the protecting group, to form eptifibatide. The invention further provides products produced by the described processes, novel compounds that can be used as synthetic intermediates for the preparation of eptifibatide, and novel compounds that are structurally similar to eptifibatide.

37 Claims, 3 Drawing Sheets

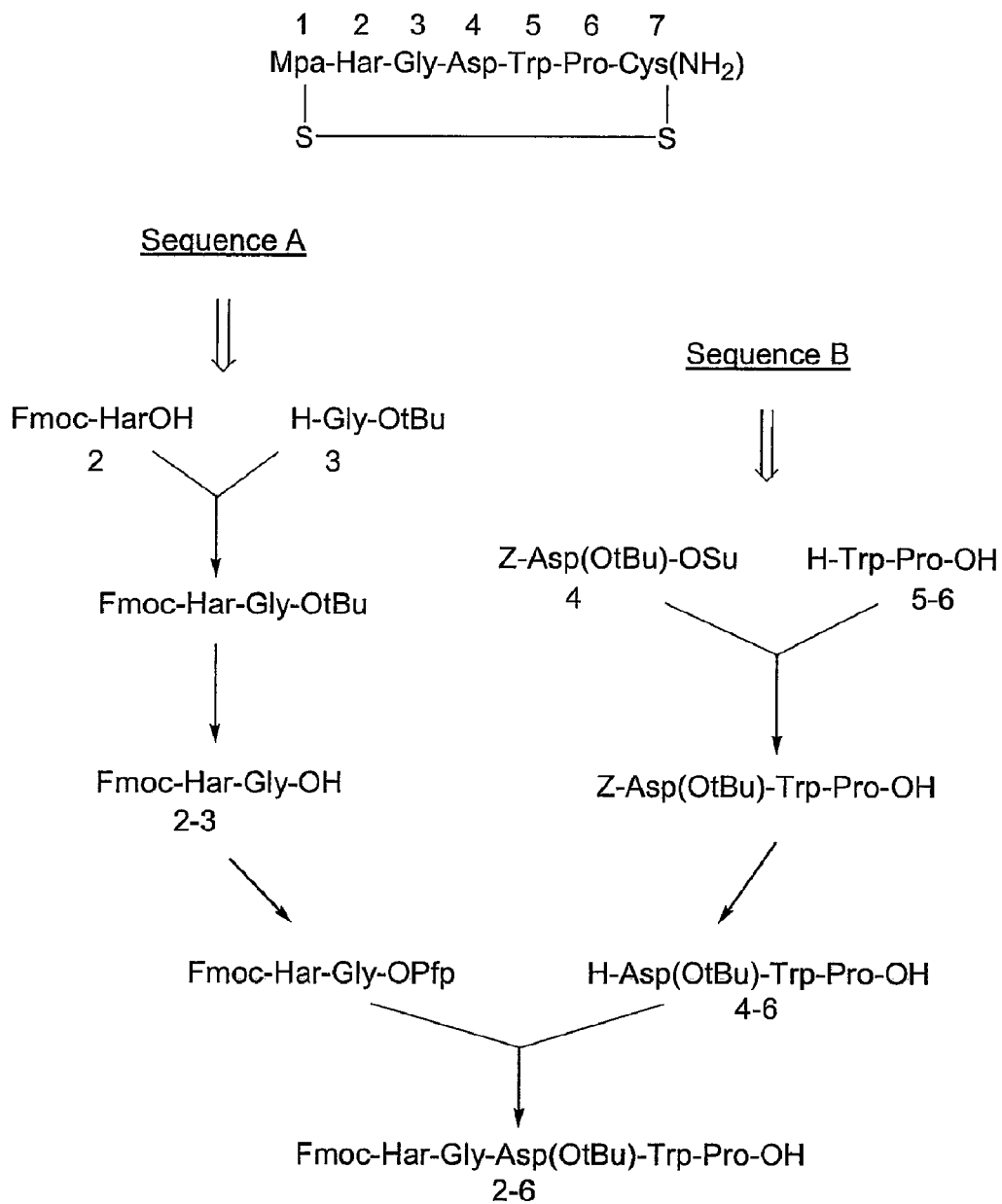
Figure 1. Preparation of the 2-6 Fragment of Eptifibatide

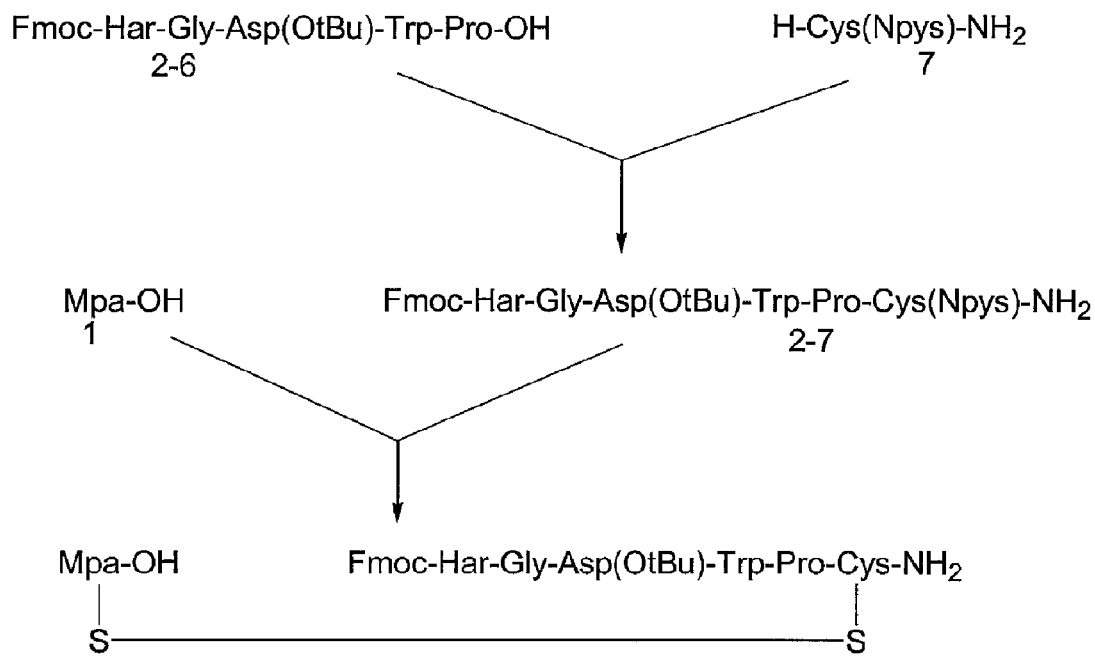
Figure 2. Preparation of Precursor A from 2-6

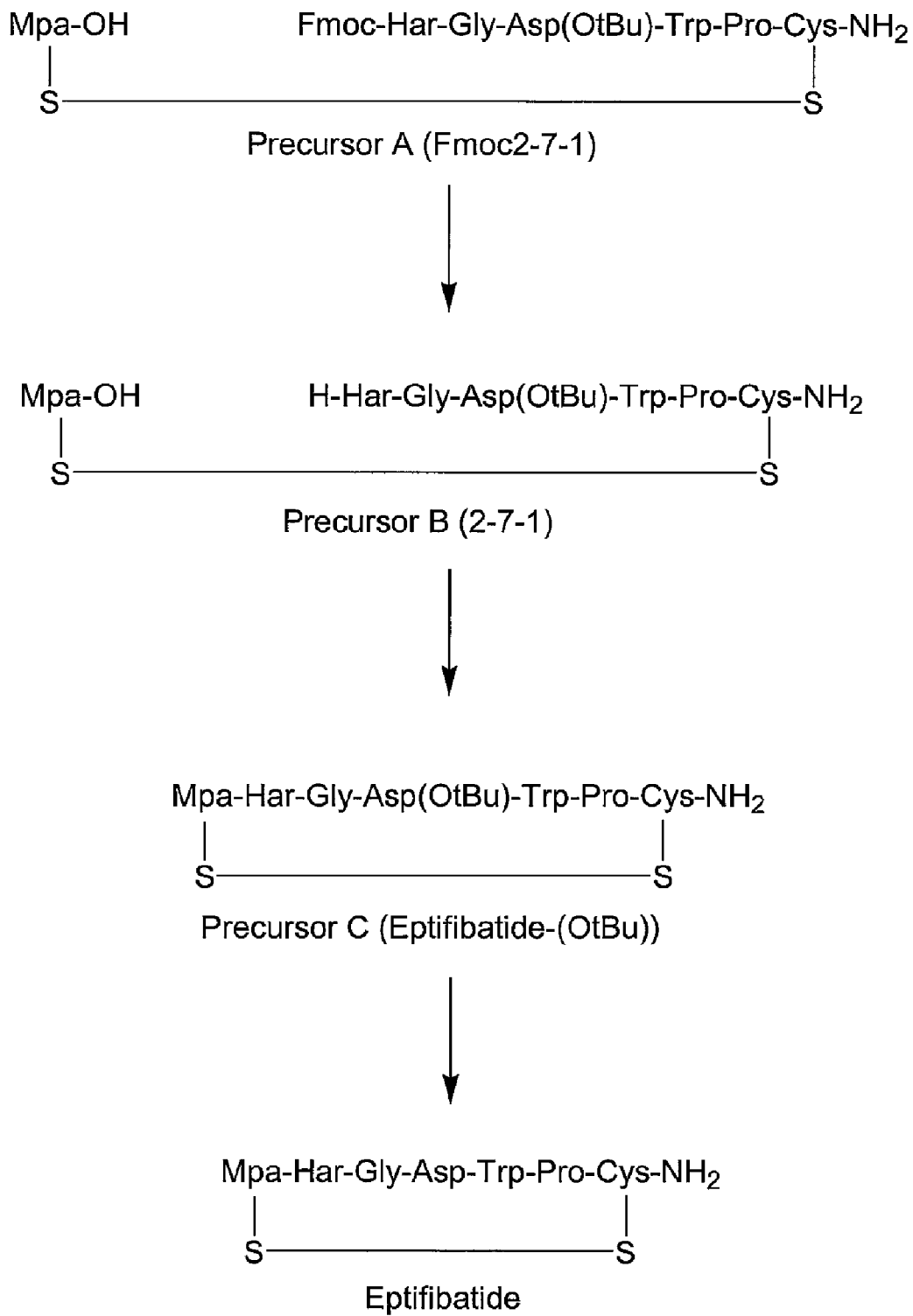
Figure 3. Preparation of Eptifibatide from Precursor A

PROCESSES FOR PREPARING EPTIFIBATIDE

CROSS REFERENCE TO RELATED APPLICATIONS

This application claims the benefit of U.S. Provisional Application No. 60/560,453, filed Apr. 8, 2004, which is incorporated herein by reference in its entirety.

FIELD OF THE INVENTION

In certain embodiments, the invention relates to novel processes for preparing eptifibatide, a drug used to treat cardiovascular disease. The invention also relates to compounds that can be used as synthetic intermediates for eptifibatide, to compounds that are structurally similar to eptifibatide, and to processes for purifying eptifibatide.

BACKGROUND OF THE INVENTION

Eptifibatide is a highly specific cyclic heptapeptide antagonist of the platelet glycoprotein IIb/IIIa. It is a short-acting parenteral antithrombotic agent that is used during percutaneous coronary interventions for the treatment of unstable angina and as an adjunct to thrombolytic agents for the treatment of acute myocardial infarction. See, for example, Phillips et al., *Journal of Biological Chemistry* (1993), 268(2), 1066-73; and Scarborough, *American Heart Journal* (1999), 138(6, Pt. 1), 1093-1104. Eptifibatide is also administered to patients undergoing balloon angioplasty, a procedure for which over 1.0 million people in the U.S. are candidates annually.

Eptifibatide is believed to work by inhibiting platelet aggregation, specifically, by blocking the platelet receptor GP IIb-IIIa. The aggregation of platelets can obstruct blood supply to the heart, causing unstable angina and, possibly, myocardial infarction (heart attack). The effects of eptifibatide are specific to platelets, avoiding interference with other normal cardiovascular processes, and the effects can be reversed when eptifibatide use is discontinued.

Eptifibatide is marketed in the U.S. under the trademark INTEGRILIN®, and is used to treat patients with acute coronary syndrome (unstable angina and non-Q-wave MI), including patients who are to be managed medically and those undergoing percutaneous coronary intervention ("PCI"). Eptifibatide is also indicated for use at the time of percutaneous coronary interventions, including procedures involving intracoronary stenting.

Many reported synthetic approaches to eptifibatide have employed known techniques of solid-phase peptide synthesis as described, for example, in U.S. Pat. Nos. 5,318,899; 5,686,570 and 5,747,447. A commercial-scale, liquid phase process was also reported at the 1999 IBC Conference on Peptide Technologies, "Peptisyntha's Method of Producing GMP Peptides on an Industrial Scale". The commercial process is a convergent synthesis involving the separate preparation of two fragments: Mpa-Har-Gly and Asp-Trp-Pro. The coupling of these two fragments provides six of the seven residues needed for eptifibatide. The last residue attached is an S-trityl-protected cysteinamide as described, for example, in U.S. Pat. No. 5,506,362. After removal of the S-trityl protecting groups (on the cysteinamide and mercaptopropionyl residues), ring closure is then achieved by disulfide bond formation. Crude eptifibatide obtained by the commercial process has a reported purity of about 80%. Two column chromatography steps improve the purity to greater than 99%.

Liquid-phase synthesis has generally been viewed as more feasible than solid-phase synthesis for the large-scale manufacture of eptifibatide. However, solubility issues and the generation of complex reaction mixtures present challenges for large-scale liquid phase processes. Complex reaction mixtures, for example, make purification of the product more difficult. Ways exist to overcome these problems, such as the use of persilylated amino acids and phase transfer reagents, as described, for example, in U.S. Pat. No. 4,954,616, and extensive chromatographic purification, but such means add to the cost of the overall process.

A need thus exists for alternative processes for the manufacture of eptifibatide.

SUMMARY OF THE INVENTION

The invention provides, inter alia, processes for preparing eptifibatide. Certain processes of the invention comprise providing a compound of formula II:

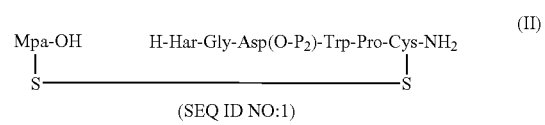

wherein Har is homoarginyl; Gly is glycyl; Asp is aspartyl; Trp is tryptophanyl; Pro is prolyl; Cys-$NH_2$ is cysteinamide; Mpa is mercaptopropionic acid; and $P_2$ is a carboxyl protecting group;

coupling the Har and Mpa residues to form a compound of formula III:

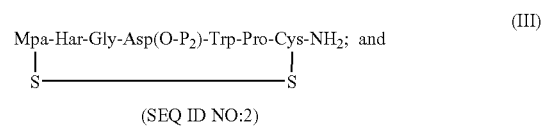

removing $P_2$ from the Asp residue of the compound of formula III to form eptifibatide.

The invention also provides processes in which an amino-terminal protected homoarginine residue is coupled with a glycine residue, thereby forming a 2-3 eptifibatide fragment of the formula:

$P_1$-Har-Gly-OH.

Also provided are processes in which an aspartic acid residue having a protected carboxyl side chain is coupled to a tryptophanyl-prolyl dipeptide through the tryptophanyl residue of the dipeptide, thereby forming a protected 4-6 eptifibatide fragment of the formula:

P$_3$-Asp(O—P$_2$)-Trp-Pro-OH.

After deprotection, the 2-3 eptifibatide fragment and the 4-6 eptifibatide fragment, in turn, can be coupled through attachment of the Gly residue of the 2-3 eptifibatide fragment to the Asp residue of the 4-6 eptifibatide fragment, thereby forming a 2-6 eptifibatide fragment of the formula:

P$_1$-Har-Gly-Asp(O—P$_2$)-Trp-Pro-OH    (SEQ ID NO:3)

wherein Har is homoarginyl; Gly is glycyl; Asp is aspartyl; Trp is tryptophanyl; Pro is prolyl; P$_1$ is an amino protecting group; and P$_2$ is a carboxyl protecting group. In preferred embodiments, the 2-6 eptifibatide fragment is coupled to an activated cysteinamide residue through the Pro residue of the 2-6 eptifibatide fragment, thereby forming a 2-7 eptifibatide fragment of the formula:

P$_1$-Har-Gly-Asp(O—P$_2$)-Trp-Pro-ACys-NH$_2$    (SEQ ID NO:4)

wherein ACys-NH$_2$ is an activated cysteinamide residue. A mercaptopropionic acid residue can be attached to the 2-7 eptifibatide fragment through a disulfide linkage between the mercaptopropionic acid residue and the ACys-NH$_2$ residue of the 2-7 eptifibatide fragment, thereby forming a compound of formula I:

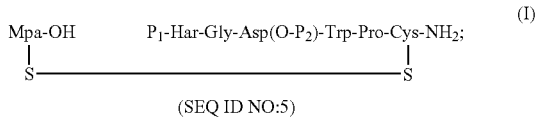

(SEQ ID NO:5)

wherein Mpa is mercaptopropionic acid; Cys-NH$_2$ is cysteinamide. Removal of P$_1$ from the Har residue of the compound of formula I provides a compound of formula II:

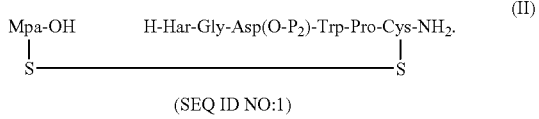

(SEQ ID NO:1)

Coupling the N-terminal Har and C-terminal Mpa residues of this compound provides a compound of formula III:

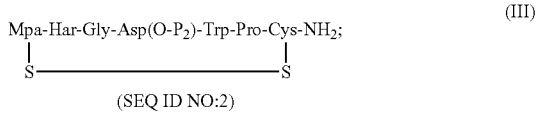

(SEQ ID NO:2)

and subsequent removal of P$_2$ from the Asp residue yields eptifibatide.

The present invention also provides products produced by the described processes, such as compounds of formula IV:

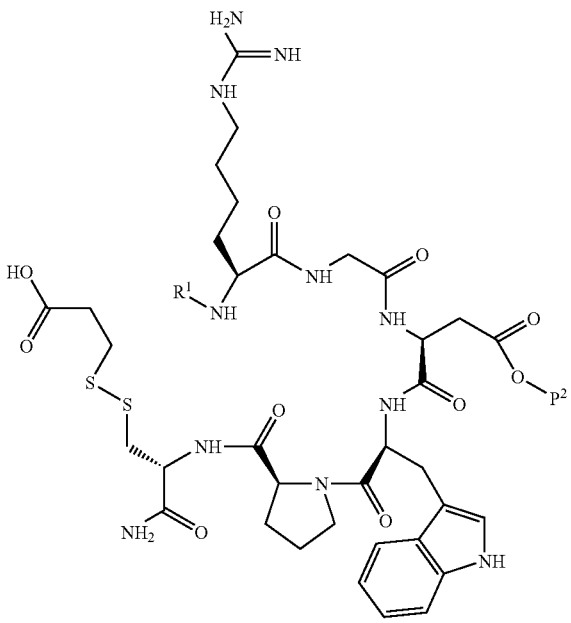

wherein R$_1$ is hydrogen or P$_1$; P$_1$ is an amino protecting group; and P$_2$ is a carboxyl protecting group. Other representative compounds of the invention include Fmoc-Har-Gly-OH, Fmoc-Har-Gly-O—P$_4$, and Fmoc-Har-Gly-Asp(O—P$_5$)-Trp-Pro-OH (SEQ ID NO:6) where P$_4$ and P$_5$ are carboxyl protecting groups. In certain embodiments, the invention provides compositions comprising eptifibatide and less than 1% of certain process impurities. The invention also provides processes for purfiying eptifibatide.

BRIEF DESCRIPTION OF THE DRAWINGS

FIG. 1 shows the preparation of the 2-6 Fragment (SEQ ID NO:8) of Eptifibatide (SEQ ID NO:7).

FIG. 2 shows the preparation of Precursor A (SEQ ID NO:10) from the 2-6 (SEQ ID NO:8) and 2-7 (SEQ ID NO:18) Fragments of Eptifibatide.

FIG. 3 shows the preparation of Eptifibatide (SEQ ID NO:7) FROM Precursor A (SEQ ID NO:10), Precursor B (SEQ ID NO:11), and Precursor C (SEQ ID NO:12).

DETAILED DESCRIPTION OF ILLUSTRATIVE EMBODIMENTS

In one aspect, the present invention provides convergent processes for preparing eptifibatide that involve preparation of a 2-3 eptifibatide fragment, preparation of a 4-6 eptifibatide fragment, and coupling of the 2-3 and 4-6 eptifibatide fragments to form a 2-6 eptifibatide fragment. Certain of these processes involve coupling the 2-6 eptifibatide fragment to an activated cysteinamide residue to form a 2-7 eptifibatide fragment, forming a disulfide bond between mercaptopropionic acid and the 2-7 eptifibatide fragment to form Precursor A, effecting intramolecular peptide coupling of Precursor A, and removing protecting groups from the coupling product to form eptifibatide.

In further embodiments, the invention relates to products produced by the described processes for preparing eptifibatide. In other embodiments, the invention relates to novel compounds that can be used as intermediates for the preparation of eptifibatide. In further embodiments, the invention relates to compounds that are structurally similar to eptifibatide. The invention also provides, in additional embodiments, processes for purifying eptifibatide.

As used herein, the term "carboxyl protecting group" refers to a moiety that can be selectively attached to and removed from a carboxyl group to prevent it from participating in undesired chemical reactions, without unacceptably adverse affects on desired reactions. Examples of carboxyl protecting groups include esters, such as methyl, ethyl, t-butyl, (un) substituted benzyl, and silyl esters, among others. Other carboxyl protecting groups are well known in the art and are described in detail in Protecting Groups in Organic Synthesis, Theodora W. Greene and Peter G. M. Wuts, 3rd Edition, 1999, published by John Wiley and Sons, Inc.

As used herein, the term "amino protecting group" refers to a moiety that can be selectively attached to and removed from a nitrogen atom to prevent it from participating in undesired chemical reactions, without unacceptably adverse affects on desired reactions. Examples of amino protecting groups include carbamates, such as Boc, Cbz, Fmoc, alloc, methyl and ethyl carbamates, among others; cyclic imide derivatives, such as phthalimide; amides, such as formyl, (un)substituted acetyl, and benzoyl; and trialkyl silyl groups, such as t-butyldimethylsilyl and triisopropylsilyl. Other amino protecting groups are well known in the art and are described in detail in Protecting Groups in Organic Synthesis, Theodora W. Greene and Peter G. M. Wuts, 3rd Edition, 1999, published by John Wiley and Son, Inc.

As used herein, the term "coupling," and all variations thereof, refers to the formation of an amide bond, by any means, between the moieties being joined.

As used herein, the term "attaching," and all variations thereof, refers to the formation of an amide or disulfide bond, by any means that can be used for form an amide or disulfide bond, between the moieties being joined.

As used herein, the term "activated cysteinamide residue" refers to a cysteinamide residue that is capable of forming a disulfide bond with mercaptopropionic acid.

As used herein, the term "Gly-eptifibatide" refers to a compound that is structurally related to eptifibatide but contains two adjacent glycine residues rather than a single glycine residue.

All amino acid residues referred to herein are natural amino acids that have the L-configuration.

Eptifibatide has the following chemical structure:

Eptifibatide can also be represented using amino acid designations as follows:

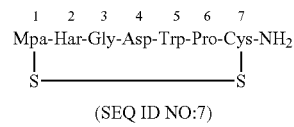

(SEQ ID NO:7)

where the amino acid designations correspond to the chemical drawing shown below:

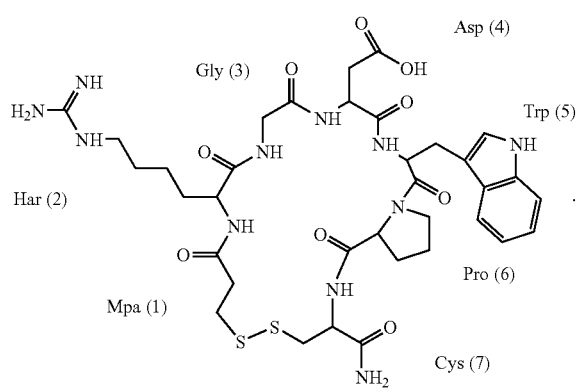

For the ease of description, the residues can also be numbered from (1) through (7). Residue (1) is mercaptopropionic acid; (2) is homoarginyl (Har); (3) is glycyl (Gly); (4) is aspartyl (Asp); (5) is tryptophanyl (Trp); (6) is prolyl (Pro); and (7) is cysteinamide (Cys-$NH_2$).

In certain embodiments, the present invention relates to convergent processes for preparing eptifibatide. In a first sequence of steps, a 2-3 eptifibatide fragment is prepared containing amino acids (2) and (3). In a second sequence, a 4-6 eptifibatide fragment is prepared containing amino acids (4), (5) and (6). The two fragments are then coupled to provide a single 2-6 fragment, which is a pentapeptide. The 2-6 fragment of eptifibatide is protected at the amino-terminal of the Har residue and at the aspartyl side chain carboxyl group. FIG. 1 outlines an exemplary process for the preparation of the 2-6 eptifibatide fragment:

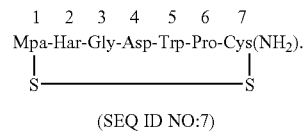

(SEQ ID NO:7)

Sequence A of FIG. 1 shows the preparation of the 2-3 eptifibatide fragment and Sequence B shows the preparation of the 4-6 eptifibatide fragment. The two sequences converge to provide the 2-6 fragment of eptifibatide. Although Scheme 1 shows exemplary amino acid protecting groups, it will be appreciated by those skilled in the art of peptide synthesis that other known amino acid protecting groups can also be used. For example, in place of the Fmoc (9-fluorenylmethoxycarbonyl) group, other carbamate protecting groups such as Cbz (benzyloxycarbonyl), RCbz (benzyloxycarbonyl groups substituted on the aromatic ring), 9(2-sulfo)fluorenylmethylcarbamate, 9(2,7-dibromo)fluorenylmethylcarbamate, 2-chloro-3-indenylmethylcarbamate, Benz[f]inden-3-ylmethylcarbamate, or Alloc (Allyloxycarbonyl) groups can be used.

The t-butyl ester on the aspartyl residue can be replaced by any other protecting group that can be cleaved by acid treatment such as, for example, ODpm (diphenylmethyl ester) or protecting groups that can be cleaved by hydrogenolysis such as, for example, OBzl (benzyl ester).

The Fmoc-Har moiety in the eptifibatide fragments depicted in Sequence A of Scheme 1 can be replaced by $R_{NP1}$-Har, where $R_{NP1}$ is an amino protecting group such as, for example, a Cbz (benzyloxycarbonyl) group, a RCbz (benzyloxycarbonyl substituted on the aromatic ring) group, or an Alloc (Allyloxycarbonyl) group. Similarly, the Z-Asp (or Cbz-Asp) moiety in the eptifibatide fragments depicted in Sequence B can be replaced by $R_{NP2}$-Asp, where $R_{NP2}$ is an amino protecting group that can be cleaved in basic conditions such as, for example, Fmoc (fluorenylmethyloxycarbonyl), or where $R_{NP2}$ is an amino protecting group that can be cleaved by hydrogenelysis such as, for example, a RCbz (benzyloxycarbonyle protecting group with substituted aromatic ring) group. In addition, the -OtBu group depicted in Scheme 1 can be replaced by $R_{CP}$, where $R_{CP}$ is a carboxyl protecting that can be cleaved by acid treatment, such as, for example, an ODpm (diphenylmethyl ester) group. Pfp (pentafluorophenyl) can be replaced by $R_{L1}$, where $R_{L1}$ is a carboxyl activating group; and Su (succinimide) can be replaced by $R_{L2}$, where $R_{L2}$ is a carboxyl activating group. Independently of the nature of the fragment, both Pfp and Su can be replaced by other stable active esters such as, for example, mono and dinitrophenyl esters, tri- and pentaphenyl ester, It will be appreciated by those skilled in the art that the selection of particular protecting groups depends upon the identity of other protecting groups that exist on the same compound. In certain embodiments of the invention, a particular protecting group is chosen so that it can be removed selectively under reaction conditions that do not affect other protecting groups.

In certain embodiments of the invention, the protected 2-6 eptifibatide fragment is next coupled to an "activated" cysteinamide (7), such as, for example, 3-nitro-2-pyridinesulfenyl-cysteinamide (H-Cys(Npys)-NH$_2$); Nps (2-nitro-phenylsulfenyl); S-phenylthiocysteinamide, where the phenyl ring is substituted; S-alkylthiocysteinamide; or the S-sulfonate and S-sulfenylthiocarbonates of cysteinamide, to form the 2-7 hexapeptide fragment of eptifibatide. The remaining eptifibatide residue is mercaptopropionic acid or Mpa-OH (1). Mpa-OH is attached to the 2-7 hexapeptide fragment under conditions that form a disulfide linkage between 1 and the 2-7 fragment. The resulting disulfide piece, designated herein as Precursor A, is a key and novel precursor for making eptifibatide. The structure of Precursor A is shown below:

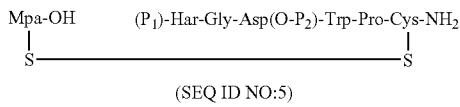

(SEQ ID NO:5)

where $P_1$ is an amino protecting group and $P_2$ is a carboxyl protecting group. Preferably the $P_2$ group is stable under conditions that are suitable for removal of the $P_1$ group. The selection of compatible $P_1$ and $P_2$ groups that allow for the selective removal of only one of the groups is well-known in the art. An example of a compatible pair of protecting groups is $P_1$=Fmoc, which may be removed under basic conditions, and $P_2$=t-butyl, which is stable under the same conditions.

FIG. 2 outlines an exemplary process for the preparation of Precursor A.

As in Scheme 1, the Fmoc and the t-butyl groups shown in Scheme 2 can be replaced by other known protecting groups that are generally recognized to be useful for peptide synthesis.

In certain embodiments of the invention, removal of the $P_1$ protecting group from Precursor A provides another precursor, Precursor B, which is the 2-7-1 portion of eptifibatide:

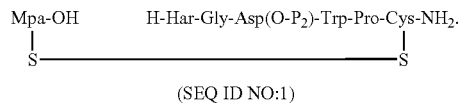

(SEQ ID NO:1)

Precursor B can be converted, via an intramolecular peptide coupling, to Precursor C:

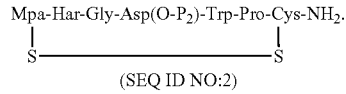

(SEQ ID NO:2)

The intramolecular peptide coupling can be effected, for example, in an organic solvent in the presence of a suitable coupling reagent such as, for example, a uronium-type coupling agent such as, but not limited to, O-[cyano(ethoxycarbonyl)methylenamino]-N,N,N',N'-tetramethyluronium tetrafluoroborate (TOTU), HBTU, or TBTU (2-(1H-Benzotriazole-1yl)-1,1,3,3-tetramethyluronium hexafluorophosphate and tetrafluoroborate respectively); a carbodiimide type reagent such as, but not limited to, DCC (dicyclohexylcarbodiimide), DIC (diisopropylcarbodiimide), or EDC (1-Ethyl-3-(3-dimethylaminopropyl)-carbodiimide); active esters; or phosphonium type coupling reagents such as, for example, Bop (benzotriazol-1-yloxy-tri(dimethylamino)-phosphonium hexafluorophosphate) or PyBOP benzotriazol-1-yloxy-tri(pyrrolidino)-phosphonium hexafluorophosphate). Peptide coupling is described, for example, in Humphrey and Chamberlin, Chem. Rev. 1997, 97, 2243-2266, incorporated herein by reference in its entirety.

Removal of the $P_2$ protecting group from Precursor C provides eptifibatide. The removal of $P_2$ can be effected, for example, in an organic solvent in the presence of acid, base or any other reagent or reagent system in which the protecting group is labile. FIG. 3 outlines an exemplary process for the preparation of eptifibatide from Precursor A.

After removal of the Fmoc protecting group, the 2-7-1 fragment undergoes an intramolecular peptide coupling to provide the t-butyl ester of eptifibatide. Removal of the t-butyl group from the aspartyl residue yields eptifibatide.

In certain embodiments, the present invention also relates to compounds that are structurally similar to eptifibatide and are prepared according to processes that are similar to the processes described above for preparing eptifibatide. Such compounds include, for example, -Gly-eptifibatide, which contains two adjacent glycine residues, rather than a single glycine residue as in eptifibatide:

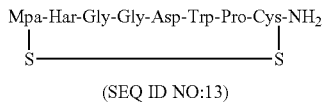

(SEQ ID NO:13)

Gly-eptifibatide can be prepared, for example, according to the procedure described above for preparing eptifibatide, except a Gly-Gly dipeptide is coupled to homoarginine to form what corresponds to the 2-3 eptifibatide fragment, rather than coupling glycine to homoarginine to form the fragment. For example, according to this modified procedure, the H-Gly-OtBu (3) group shown in Scheme 1 is replaced with H-Gly-Gly-OtBu.

Gly-eptifibatide is also produced, in some embodiments of the invention, during the preparation of eptifibatide according to the methods described above for preparing eptifibatide. Certain embodiments of the invention relate to compositions comprising eptifibatide and Gly-eptifibatide, including compositions comprising at least 99% eptifibatide and Gly-eptifibatide in the range of about 0.01% to about 1% and compositions comprising at least 99% eptifibatide and Gly-eptifibatide in the range of about 0.01% to about 0.1%.

The present invention also provides methods for purifying eptifibatide that comprise, for example, contacting an eptifibatide solution with a stationary phase that comprises, for example, octadecyl carbon chains attached to silica, washing the stationary phase contacted with the eptifibatide solution with a trifluoroacetic acid/acetonitrile solution, optionally washing the stationary phase contacted with the eptifibatide solution with an acetic acid/acetonitrile solution, and washing stationary phase contacted with the eptifibatide solution with an ammonium acid/acetonitrile solution. Reverse stationary phases are well known to those skilled in the art, and other of such phases can be substituted for octadecyl carbon-based silica.

In particular embodiments of the invention, the stationary phase contacted with the eptifibatide solution is washed with a gradient having initial concentrations of 95% of a 0.1% aqueous trifluoroacetic acid solution and 5% of an acetonitrile solution, and final concentrations of 50% of a 0.1% aqueous trifluoroacetic acid solution and 50% of an acetonitrile solution.

The invention provides further embodiments in which the stationary phase contacted with the eptifibatide solution is washed with a gradient having initial concentrations of 95% of a 0.5% aqueous solution of acetic acid and 5% of an acetonitrile solution, and final concentrations of 50% of a 0.5% aqueous solution of acetic acid and 50% of an acetonitrile solution. In some embodiments, the stationary phase is washed with the acetic acid/acetonitrile gradient following one or more washes with a trifluoroacetic acid/acetonitrile gradient.

The invention also provides embodiments in which the ammonium acid/acetonitrile solution is a solution comprising 95% of an aqueous 100 mM ammonium acid solution and 5% of an acetonitrile solution. In certain aspects of the invention, the stationary phase is washed with an ammonium acid/acetonitrile solution following washing with a trifluoroacetic acid/acetonitrile gradient and/or an acetic acid/acetonitrile gradient.

The coupling of the amino acid residues that occurs in the described processes can be accomplished through known methods of peptide synthesis that are familiar to those skilled in the art. Any suitable coupling procedure for forming peptides can be employed.

The following examples are illustrative of certain embodiments of the invention and should not be considered to limit the scope of the invention.

EXAMPLE 1

Preparation of Z-Asp(OtBu)-Trp-Pro-OH

Z-Asp(OtBu)-Trp-Pro-OH was obtained by known procedures starting with the commercially available Z-Asp(OtBu)-OSu and H-Trp-Pro-OH as described, for example, in Bodanszky, M. (1979), Active esters in peptide synthesis, *The peptides*, Vol. 1 (ed. E. Gross and J. Meienhofer), Chapter 3. Academic Press, London, which is incorporated herein by reference in its entirety.

EXAMPLE 2

Preparation of H-Asp(O-tBu)-Trp-Pro-OH

To a 2 liter reactor charged with dimethylacetamide (DMAC, 1.2 L) at a temperature of about 20° C. was added 0.300 kg of starting material Z-Asp(OtBu)-Trp-Pro-OH, maintaining the temperature at about 20° C. The Z-Asp(OtBu)-Trp-Pro-OH was allowed to dissolve and the reaction mixture was then purged and blanketed by a nitrogen atmosphere. Palladium on carbon (5 weight %) (0.015 kg) was added to the reaction mixture, followed by hydrogenation at a 2 bar pressure while the reaction mixture was maintained at about 20° C.

After two hours, and every hour thereafter, a sample from the reaction was analyzed by HPLC. HPLC analysis was conducted on Purospher Star C18 55*4 mm column with a water/acetonitrile solvent mixture containing 0.1% trifluoroacetic acid (TFA) with a gradient of 98:2 water/acetonitrile to 2:98 water/acetonitrile in 10 minutes. HPLC detection was at 215 nm, flow was 2.0 mL/min, and the temperature was 40° C.

The reaction was considered to be complete when the HPLC analysis showed the starting material to be less than or equal to 0.2% relative to the product area percent. When the reaction was shown to be complete by HPLC, an aqueous solution of p-toluenesulfonic acid (0.094 kg p-TsOH in 0.150 L of water) was added to the reaction mixture. The reaction mixture was then filtered through Celite® that was pre-washed with DMAC (Celite® washed three times with 0.6 L). After filtration of reaction mixture, the filter cake was washed three times with fresh DMAC (0.3 L). HPLC analysis after the last wash was performed to confirm that no product remained in the filter cake.

The combined filtrates were transferred to a new vessel at about 20° C., at which temperature N-ethylmorpholine (0.066 L) was added. The temperature was maintained below about 22° C. during the addition. The mixture was then cooled to about 8-12° C. and water (3 L) was added slowly so as to maintain the temperature below about 15° C. The mixture was then stirred at about 8-12° C. for about 30 minutes and held at that temperature for 8 hours. During this time the product crystallized out of solution. The supernatant can be analyzed by HPLC to determine the amount of product still in solution and whether further cooling is necessary. The slurry obtained was filtered and the collected solids were washed twice with a 2:1 solution of water:DMAC (0.9 L each). The solids were then washed twice with acetonitrile (0.9 L each) and dried under a vacuum below about 25° C. until at a constant weight. The water content after drying was 3.5% (Karl-Fisher analysis).

The product was analyzed by reverse phase HPLC using an aqueous trifluoroacetic acid/acetonitrile gradient.

A LC/MS analysis confirmed the mass [M+H] 473.0 of H-Asp(O-tBu)-Trp-Pro-OH.

The recovery yield was 93.2% (0.218 kg); the net yield was 93.1% (based on nitrogen content: 95.4%).

EXAMPLE 3

Preparation of Fmoc-Har-Gly-Asp(O-tBu)-Trp-Pro-OH (SEQ ID NO:8)

To a slurry of Fmoc-Har-Gly-OH (0.163 kg net ; based on peptide content: 90.5%) in THF:DMAC (0.717 L and 0.179 L respectively) was added methanesulfonic acid (0.027 L) and pentafluorophenol (0.083 kg). The mixture was stirred at about 20° C. until the solid dissolved. N-ethylmorpholine (NEM) (0.030 L) was added drop wise, followed by dicyclohexylcarbodiimide (DCC) (0.072 kg) in THF (0.179 L) and the mixture was stirred at about 20° C. The formation of Fmoc-Har-Gly-OPfp was followed by HPLC assay. After about 17 hours, the ratio of Fmoc-Har-Gly-OH/Fmoc-Har-Gly-OPfp was 1.5/98.5.

To the reaction mixture was added H-Asp(O-tBu)-Trp-Pro-OH (0.146 kg, about 3.5 w/w % $H_2O$) and NEM (0.049 L). The mixture was stirred at about 20° C. for 3 hours. At that time, HPLC analysis showed the mixture to contain about 87% of product, <2% Fmoc-Har-Gly-OPfp, 6% of Fmoc-Har-Gly-OH, about 0.5% of H-Asp(O-tBu)-Trp-Pro-OH, and about 5.5% of an impurity that was identified as Fmoc-Har-Gly-Asp(O-tBu)-Trp-Pro-Asp(O-tBu)-Trp-Pro-OH (SEQ ID NO:15) ("d.a. impurity"). HPLC analysis was conducted on a Purospher Star C18 55*4 mm column with a water/acetonitrile solvent mixture containing 0.1% trifluoroacetic acid (TFA) with a gradient of 98:2 water/acetonitrile to 2:98 water: acetonitrile in 10 minutes. HPLC detection was at 215 nm, flow was 2.0 mL/min and temperature was 40° C.

The reaction mixture was filtered and the solid was washed twice with a 5/1 mixture of THF/DMAC (2×0.489 L). The filtrate was concentrated to about 0.815 L at no more than 35° C. under reduced pressure (about 20 mBar). The concentrated mixture was added slowly over 1 h to ¼ mixture of acetonitrile/H2O (4.1 L) containing sodium bicarbonate (0.059 kg). The addition rate was carefully controlled to avoid formation of a gummy precipitate. About 3.5% of the solution was added over about 15 min, and the addition was interrupted to stir the slurry at about 20° C. for 1 h. The pasty precipitate turned to white slurry. 7.5 extra % of the solution was added over 15 to 30 min, and the addition was interrupted again to stir the slurry at about 20° C. for 2 h. The remaining 89% of solution was added over about 2 h. The mixture was stirred at about 20° C. for 12 h then filtered. The solid was washed with a ¼ mixture of acetonitrile/H2O (3×0.7 L), a ⅔ mixture of acetonitrile/di-isopropylether (DIPE) (3×0.7 L) and DIPE (2×0.7 L). The solid product was dried at T≦30° C. until a constant weight was achieved. The water content after drying was 3.3% (Karl-Fisher analysis).

The product was analyzed by reverse phase HPLC using an aqueous trifluoroacetic acid/acetonitrile gradient.

A LC/MS analysis confirmed the mass [M+H] 922.5 of Fmoc-Har-Gly-Asp(OtBu)-Trp-Pro-OH (SEQ ID NO: 8).

The recovery yield was 81.8% (0.234 kg); the net yield was 82.3% (based on nitrogen content: 96.0%).

EXAMPLE 4

Preparation of Fmoc-Har-Gly-Asp(O-tBu)-Trp-Pro-Cys(NPys)-$NH_2$ (SEQ ID NO:9)

In a reactor charged with peptide synthesis grade DMF (0.675 L) at about 20° C. was added Fmoc-Har-Gly-Asp(OtBu)-Trp-Pro-OH (0.225 kg). The mixture was cooled to about 0° C., and H-Cys(NPys)-$NH_2$ was added as the solid hydrochloride salt (0.080.kg). O-Benzotriazol-1-yl-N,N,N', N'-tetramethyluronium tetrafluoroborate (TBTU) (0.082 kg) was added to the reaction mixture. The pH of the reaction mixture was adjusted to 6.5 to 7.0 by the portion-wise addition of diisopropylethylamine (DIPEA) (0.112 L), while maintaining the temperature at about 0° C. The mixture was stirred at that temperature, during which time samples were analyzed by HPLC for product formation about every 45 minutes. The pH of the reaction mixture was maintained at pH 6.5 to 7.0 with the addition of DIPEA as needed. HPLC analysis was conducted on a Platinum EPS 100-5 C18 5µ 250*4.6 mm column; Solvent A: TFA 0.1% in water; Solvent B: TFA 0.1% in acetonitrile; gradient: 12 to 98% B in 15 minutes. HPLC detection was at 215 nm, flow 2.0 mL/min and the temperature was 40° C. The reaction was considered complete when the pentapeptide and Cys(NPys)-$NH_2$ starting materials were each shown to be less than 1% by HPLC. Otherwise, additional TBTU, DIPEA and the starting material shown to be deficient in the mixture were added.

The reaction mixture was added to another vessel that contained water (4.5 L) at a temperature of about 5° C. This temperature was maintained during the addition with stirring. After stirring for 10 minutes at about 5° C., the mixture was filtered and the solid was washed five times with water (0.9 L each). The solid was then washed three times with toluene (0.675 L each). The washes with toluene can be replaced by washes with diisopropyl ether. The solid was dried under vacuum at 35° C. or below until a constant weight was achieved. The water content after drying was 1.2% (Karl-Fisher analysis).

The product was analyzed by reverse phase HPLC using an aqueous trifluoroacetic acid/acetonitrile gradient.

A LC/MS analysis confirmed the mass [M+H] 1178.4 of Fmoc-Har-Gly-Asp(O-tBu)-Trp-Pro-Cys(NPys)$NH_2$ (SEQ ID NO:9).

The recovery yield was 102.4% (0.295 kg) and the net yield 87.7% (based on peptide content: 82.0%).

EXAMPLE 5

Preparation of Fmoc-Har-Gly-Asp(O-tBu)-Trp-Pro-Cys($NH_2$)-Mpa (SEQ ID NO:16)(Fmoc[2-7-1])

In a reactor charged with HPLC grade acetonitrile (0.570 L) and peptide synthesis grade DMF (0.285 L), under a nitrogen atmosphere at about 20° C., was added 0.285 kg of Fmoc-Har-Gly-Asp(O-tBu)-Trp-Pro-Cys(NPys)$NH_2$ (SEQ ID NO:9) (Fmoc[2-7]) slowly with agitation. After dissolution of the Fmoc[2-7], the mixture was cooled to about −3° C. A solution of mercaptopropionic acid (Mpa, 0.023 kg) in acetonitrile (0.057 L), prepared at about 20° C., was added to the reaction mixture at such a rate as to maintain the reaction temperature at about −3° C. The reaction was monitored by HPLC analysis and considered completed when the analysis showed less than 1% of Fmoc[2-7] compared to Fmoc[2-7-1]. HPLC analysis was conducted on a Purospher Star C18 55*4 mm column with a water/acetonitrile solvent mixture containing 0.1% trifluoroacetic acid (TFA) with a gradient of 98:2 water/acetonitrile to 2:98 water:acetonitrile in 10 minutes. HPLC detection was at 215 nm, flow was 2.0 mL/min and the temperature was 40° C.

The reaction mixture was added to a second vessel that was charged with HPLC grade acetonitrile (5.7 L) and N-ethylmorpholine (NEM, 0.033 L) at about 20° C. After the addition was complete, the reaction was stirred at that temperature for about 30 minutes. The slurry was slowly cooled to about 0° C. and stirring was continued at that temperature for about 45 minutes. The following procedure was then performed three times: (a) the agitation was stopped to allow for the precipitate and the supernatant to separate; (b) the supernatant was pumped out of the vessel (c) at about 0° C., fresh HPLC grade acetonitrile (1.425 L) was added to the reactor and agitation was re-started; and (d) the slurry was stirred for about 5 minutes at about 0° C. The remaining slurry was filtered, and the solid was washed twice with HPLC grade acetonitrile (1.140 L each) and once with toluene (1.425 L). The wash with toluene can be replaced by a wash with diisopropyl ether. The solid was dried under high vacuum at no more than 20° C.

The product was analyzed by reverse phase HPLC using an aqueous trifluoroacetic acid/acetonitrile gradient.

A LC/MS analysis confirmed the mass [M+H] 1128.4 of Fmoc-Har-Gly-Asp(O-tBu)-Trp-Pro-Cys($NH_2$)-Mpa (SEQ ID NO:16).

The recovery yield was 93.8% (0.256 kg); the net yield was quantitative (based on peptide content: 87.4%).

EXAMPLE 6

Preparation of H-Har-Gly-Asp(O-tBu)-Trp-Pro-Cys($NH_2$)-Mpa (SEQ ID NO:17) ([2-7-1])

To a reactor charged with peptide synthesis grade DMF (0.750 L) at about 20° C., was added 0.250 kg of Fmoc-Har-Gly-Asp(O-tBu)-Trp-Pro-Cys($NH_2$)-Mpa (SEQ ID NO:16) (Fmoc[2-7-1]) slowly with agitation. The mixture was cooled to about 10° C., at which temperature diethylamine (0.034 L) was added. After addition of the diethylamine, the temperature of the mixture was allowed to rise to about 20° C. Progress of the reaction was monitored by HPLC analysis of samples taken every hour. HPLC analysis was conducted on a Platinum EPS 100-5 C18 5µ 250*4.6 mm column; Solvent A: TFA 0.1% in water; Solvent B: TFA 0.1% in acetonitrile; gradient: 22 to 98% B in 15 minutes. HPLC detection was at 215 nm, flow was 2.0 mL/min and the temperature was 40° C. The reaction was considered complete when the percent of Fmoc[2-7-1] was less than about 0.5% with respect to [2-7-1]. The reaction was usually complete in 3 hours.

The reaction mixture was added to a second vessel charged with ethyl acetate (5.0 L) and cooled to about 10° C. The resulting suspension was stirred for 10 minutes at about 10° C. The following procedure was then performed twice: (a) the agitation was stopped and the precipitate was allowed to separate from the supernatant for about 15 minutes; (b) the supernatant was pumped out of the vessel; (c) fresh ethyl acetate (0.750 L) was added at about 10° C.; (c) the suspension was stirred at about 10° C. for about 5 minutes. The slurry was filtered and the solid was washed 6 times with ethyl acetate (0.750 L each time). Additional washes with diisopropyl ether can be performed to remove the residues of ethyl acetate. The solid was dried under high vacuum at no more than 25° C. for a maximum of 18 hours.

The product was analyzed by reverse phase HPLC using an aqueous trifluoroacetic acid/acetonitrile gradient.

A LC/MS analysis confirmed the mass [M+H] 906.3 of H-Har-Gly-Asp(O-tBu)-Trp-Pro-Cys($NH_2$)-Mpa (SEQ ID NO:17).

A GC analysis showed 3.4% residual diethylamine.

The recovery yield was 106.1% (0.213 kg) and the net yield 99.2% (based on peptide content: 81.9%).

EXAMPLE 7

Preparation of [MPA-Har-Gly-Asp(O-tBu)-Trp-Pro-Cys]($NH_2$) (SEQ ID NO:12) (cyclo-[1-7](OtBu)-$NH_2$)

To the reactor was charged peptide synthesis grade DMF (0.768 L) and the solution was cooled to about 10° C. O-[cyano(ethoxycarbonyl)methylenamino]-N,N,N',N'-tetramethyluronium tetrafluoroborate (TOTU) (0.070 kg) was added followed by dilution with peptide synthesis grade dichloromethane (1.536 L) while maintaining the temperature below 15° C. The resulting solution was cooled to about −6° C. and NEM (0.024 L) was added in small portions maintaining the temperature at about −6° C. The pH was measured before and after the addition of NEM. A sample was taken for HPLC analysis.

HPLC analysis was on a Phenomenex Luna C18(2) column, 5um, 150*4.6 mm, gradient 12 to 98% B in 15 minutes. Solvent A: TFA 0.1% in water, Solvent B: TFA 0.1% in acetonitrile. Detection was at 215 nm, the flow was 2 mL/min and the temperature was 40° C.

To a separate reactor was charged peptide synthesis grade DMF (0.768 L) at about 20° C. followed by 0.192 kg of H-Har-Gly-Asp(O-tBu)-Trp-Pro-Cys($NH_2$)-Mpa (SEQ ID NO:17)([2-7-1]). When the solid dissolved, the resulting solution was cooled to about 0° C. HOBt (0.026 kg) was added in small portions (weight of HOBt was corrected for purity). The resulting solution was diluted with peptide synthesis grade dichloromethane (0.384 L). A sample was taken for HPLC analysis.

The solution of [2-7-1] was added into the solution of TOTU very slowly with an addition pump over a minimum of 3 hours while the temperature was maintained at about −6° C. A sample was taken after the addition of 50% of the [2-7-1] solution for HPLC analysis. The pH was also measured at this point. HPLC and pH samples were also taken when [2-7-1] addition was complete. The pH was adjusted to 7-7.5 by the addition of NEM if needed, while the temperature was maintained at about −6° C.

The pH was checked every 15 minutes and was adjusted to 7-7.5 as necessary with NEM while the temperature was maintained at about −6° C. A sample was taken for HPLC every 45 minutes until the cyclization was complete. The reaction was considered complete when the area percent of [2-7-1] was <0.5% relative to cyclized product.

If the reaction stalled, 1.1 equivalents of TOTU per residual amount of [2-7-1] were added and the pH was adjusted to 7-7.5 as needed while the temperature was maintained at −6° C.

When the reaction was complete, the mixture was concentrated under a vacuum at <40° C. to a final volume of about 0.8 L. The resulting viscous solution was cooled to about 5° C. and added slowly to rapidly stirring ethyl acetate that was at about 0° C. (7.0 L) The resulting slurry was stirred at about 0° C. for 20 minutes. The following procedure was then performed three times: (a) the agitation was stopped to allow for the precipitate and supernatant to separate; (b) the supernatant was pumped out of the vessel; (c) at about 0° C., fresh ethyl acetate (1.15 L) was added to the reactor and agitation was re-started; (d) the slurry was stirred for about 20 minutes at about 0° C. The final time the above procedure was performed, a smaller volume of ethyl acetate (0.768 L) was added to the reaction and agitation was re-started for 10 minutes at 0° C. The resulting slurry was filtered and the solid was washed once with ethyl acetate (0.576 L) and three times with di-isopropyl ether (0.576 L). The solid was dried under a high vacuum at about 25° C.

The product was analyzed by reverse phase HPLC using an aqueous trifluoroacetic acid/acetonitrile gradient.

A LC/MS analysis confirmed the mass [M+H] 888.2 of (cyclo-[1-7](OtBu)-NH$_2$).

The recovery yield was 103.7% (0.194 kg); the net yield was quantitative (based on peptide content: 79.7%).

EXAMPLE 8

Preparation of [MPA-Har-Gly-Asp-Trp-Pro-Cys](NH$_2$) (SEQ ID NO:7) cyclo-[1-7]-NH$_2$)

A mixture of dichloromethane (0.573 L), anisol (0.086 L) and TFA (0.122 L) was prepared at about 20° C. The resulting solution was cooled to 15° C. and solid [1-7](OtBu)-NH$_2$ (0.191 kg) was added slowly. The temperature was held below 20° C. during the addition of [1-7](OtBu)-NH$_2$. The reaction mixture was further cooled to 10° C. and an extra portion of TFA (0.365 L) was added in about 10 minutes. The temperature was held below 20° C. during the addition. After the addition of all the TFA, the reaction was allowed to stir at 20° C. and followed by HPLC.

HPLC analysis was conducted on a Platinum EPS 100-5 C18 column, 250*4.6 mm. The gradient was 22 to 98% B in 15 minutes where solvent A was 0.1% TFA in water and solvent B was 0.1% TFA in acetonitrile. Detection was at 215 nm, the flow was 1.5 mL/minute, and the temperature was 40° C. The reaction was complete when <3.0 Area % [1-7](OtBu)-NH$_2$ remained relative to the product.

When the reaction was complete the mixture was cooled to 10° C. and added to a solution of 2/1 di-isopropyl ether (DIPE)/acetonitrile (3.78 L) at 10° C. The resulting slurry was stirred for 10 minutes at 10° C. and then filtered under vacuum. The solid was washed three times with a 7/3 mixture of DIPE and acetonitrile (0.573 L) and three times with DIPE (0.573 L). The product was dried at no more than 25° C.

The product was analyzed by reverse phase HPLC using an aqueous trifluoroacetic acid/acetonitrile gradient.

A LC/MS analysis confirmed the mass [M+H] 832.3 of (cyclo-[1-7]-NH$_2$).

The recovery yield was 0.157 kg (87.9%) and the net yield was 87.2% (based on peptide content: 79.1%).

The content in pure API was 45.8%. This value was obtained by the following HPLC method: Synergi Max-RP 4 μm 80 Å 250*4.6 mm; solvent A: 52 mM H$_3$PO4/CH$_3$CN/100 mM H7SA (86/14/0.80); Solvent B: 52 mM H$_3$PO4/CH$_3$CN /100 mM H7SA (50/50/0.80); 220 nm; 1.3 ml/min; 50° C.; gradient: 0% B over 45 minutes, then to 45% B over 13 minutes, then to 100% B over 1 minute.

EXAMPLE 9

Purification of Eptifibatide

Primary-Purification:

The primary purification was a trifluoroacetic acid/acetonitrile-based purification. The norms applied for the individual main fractions were ≧92.0%. The stationary phase was a Kromasil C18, 10 μm, 100 A column with a 5 cm diameter. The column pressure was 50 bars, the flow rate was 50 ml/min, and the detection wavelength was 215 nm. The mobile phases were as follows:

Solvent A: TFA 0.1% in processed water/CH$_3$CN (95/5); and

Solvent B: TFA 0.1% in processed water/CH$_3$CN (50/50).

The column was equilibrated by elution of 100% solvent A over 15 minutes. The purification gradient was as follows: elution of 100% solvent A over 10 minutes; gradient: 15% B to 45% B over 60 minutes; and elution of 100% solvent B over 15 minutes.

The purification was monitored using method MAD-009-SF323TG1 and the target acceptance criteria were as follows:
 Main fraction (F1): ≧92%; and
 Side fraction (Fp): ≧60% and <92%.

The collected fractions were stored at 2° C. to 8° C.

Secondary Purification:

The secondary purification was an acetic acid/acetonitrile based purification. The norms for the individual main fractions were ≧99.0% with single impurities <0.3/0.5%. The stationary phase was a Kromasil C18, 10 μm, 100 A column with a diameter of 5 cm. The column pressure was 40±5 bars, the flow rate was 50 ml/min, and detection was at a wavelength of 215 nm. The mobile phases were as follows:
 Solvent A: AcOH 0.5% in processed water/CH$_3$CN (95/5); and
 Solvent B: AcOH 0.5% in processed water/CH$_3$CN (50/50).

The column was equilibrated by elution of 100% solvent A over 15 minutes. The purification gradient was as follows: elution of 100% solvent A over 10 minutes; gradient: 0% B to 15% B over 5 minutes; 15% B to 35% B over 60 minutes; and elution of 100% solvent B over 15 minutes.

The purification was monitored using method MAD-009-SF323TG1 and the target acceptance criteria were as follows:
 Main fraction (F1): ≧99.0% with impurities <0.3/0.5%; and
 Side fraction (Fp): >80.0% and <99.0%.

The collected fractions were stored at 2° C. to 8° C.

Desalting/Concentration:

A double desalting step in ammonium acetate solution was performed before the concentration step to remove the residual trifluoroacetate counter ion and to obtain the acetate form of the peptide. The concentration step reduced the volume of the processed solution.

The stationary phase for the NH$_4$OAc desalting/AcOH concentration was a Kromasil C18, 10 μm, 100 A column with a diameter of 5 cm. The column pressure was 40±5 bars, the flow rate was 50 ml/min, and the detection wavelength was 215 nm. The mobile phases were as follows:
 Solvent A: AcOH 0.5% in processed water/CH$_3$CN (95/5);
 Solvent B: AcOH 0.5% in processed water/CH$_3$CN (50/50); and
 Solvent C: NH$_4$OAc 100 mM pH: 6.5 in processed water/CH$_3$CN (95/5).

The column was equilibrated by elution of 100% solvent A over 15 minutes. For column loading, the main fraction from the AcOH purification was diluted with 2 volumes of processed water.

The desalting was preformed as follows: 10 minutes of solvent A; 10 minutes of solvent C; 10 minutes of solvent A; and 10 minutes of solvent C.

Concentration was preformed as follows: 10 minutes of solvent A and 50% B over 15 minutes.

The desalting and concentration were monitored using method MAD-009-SF323TG1 and the target acceptance criteria were as follows:
 Main fraction (F1): ≧99.0% with impurities <0.3/0.5%; and
 Side fraction (Fp): >80.0% and <99.0%.

The collected fractions were stored at 2° C. to 8° C.

The entire disclosure of each patent, patent application, and publication cited or described in this document is hereby incorporated herein by reference.

What is claimed:

1. A process for making a compound of formula III

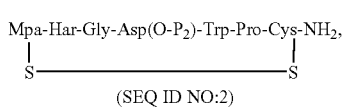

(SEQ ID NO:2)

comprising:

coupling the Har and Mpa of a compound of formula II:

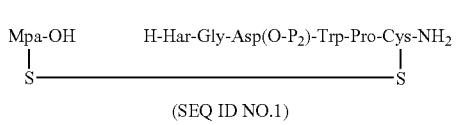

(SEQ ID NO.1)

wherein

Har is homoarginyl;

Gly is glycyl;

Asp is aspartyl;

Trp is tryptophanyl;

Pro is prolyl;

Cys-NH$_2$ is cysteinamide;

Mpa is mercaptopropionic acid; and

P$_2$ is a carboxyl protecting group; and thereby forming a compound of formula III.

2. The process of claim 1 wherein P$_2$ is t-butyl.

3. The process of claim 1 further comprising removing P$_2$ from the Asp of the compound of formula III to form eptifibatide.

4. The process of claim 1 further comprising removing $P_1$ from the Har of a compound of formula I:

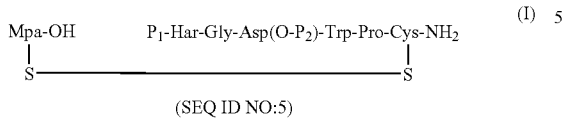

(SEQ ID NO:5)

wherein $P_1$ is an amino protecting group, thereby forming the compound of formula II.

5. The process of claim 4 wherein $P_2$ is stable under conditions suitable for removal of $P_1$.

6. The process of claim 4 wherein $P_2$ is t-butyl.

7. The process of claim 4 wherein $P_1$ is 9-fluorenylmethoxycarbonyl or benzyloxycarbonyl.

8. The process of claim 4 further comprising attaching an Mpa to a 2-7 eptifibatide sequence of the formula:

$P_1$-Har-Gly-Asp(O—$P_2$)-Trp-Pro-ACys-NH$_2$     (SEQ ID NO:4)

wherein ACys-NH$_2$ is an activated cysteinamide, through a disulfide linkage between the Mpa and the ACys-NH$_2$ of the 2-7 eptifibatide sequence, thereby forming the compound of formula I.

9. The process of claim 8 further comprising coupling a 2-6 eptifibatide sequence of the formula:

$P_1$-Har-Gly-Asp(O—$P_2$)-Trp-Pro-OH     (SEQ ID NO:3)

to an activated cysteinamide through the Pro of the 2-6 eptifibatide sequence, thereby forming the 2-7 eptifibatide sequence.

10. The process of claim 9 wherein the activated cysteinamide is H-Cys(Npys)-NH$_2$.

11. The process of claim 9 further comprising coupling a 2-3 eptifibatide sequence of the formula:

$P_1$-Har-Gly-OH and a 4-6 eptifibatide sequence of the formula:

H-Asp(O—$P_2$)-Trp-Pro-OH through attachment of the Gly of the 2-3 eptifibatide sequence to the Asp of the 4-6 eptifibatide sequence, thereby forming the 2-6 eptifibatide sequence.

12. The process of claim 11 further comprising coupling an amino-terminal protected Asp having a protected carboxyl side chain to a Trp-Pro dipeptide through the Trp of the dipeptide and removing the amino-terminal protecting group from the Asp to form the 4-6 eptifibatide sequence.

13. The process of claim 12 further comprising coupling an amino-terminal protected Har and a protected or unprotected Gly to form the 2-3 eptifibatide sequence.

14. A process comprising:
coupling an amino-terminal protected homoarginine and a protected or unprotected glycine, thereby forming a 2-3 eptifibatide sequence of the formula:

$P_1$-Har-Gly-OH;

coupling an amino-terminal protected aspartic acid having a protected carboxyl side chain to a tryptophan-proline dipeptide through the tryptophan of the dipeptide, and removing the amino-terminal protecting group from the aspartic acid, thereby forming a protected 4-6 eptifibatide sequence of the formula:

$P_3$-Asp(O—$P_2$)-Trp-Pro-OH;

coupling the 2-3 eptifibatide sequence and the 4-6 eptifibatide sequence through attachment of the Gly of the 2-3 eptifibatide sequence to the Asp of the 4-6 eptifibatide sequence, thereby forming a 2-6 eptifibatide sequence of the formula:

$P_1$-Har-Gly-Asp(O—$P_2$)-Trp-Pro-OH     (SEQ ID NO:3)

wherein
Har is homoarginyl;
Gly is glycyl;
Asp is aspartyl;
Trp is tryptophanyl;
Pro is prolyl;
$P_1$ and $P_3$ are amino protecting groups; and
$P_2$ is a carboxyl protecting group;

coupling the 2-6 eptifibatide sequence to an activated cysteinamide through the Pro of the 2-6 eptifibatide sequence, thereby forming a 2-7 eptifibatide sequence of the formula:

$P_1$-Har-Gly-Asp(O—$P_2$)-Trp-Pro-ACys-NH$_2$     (SEQ ID NO:4)

wherein ACys-NH$_2$ is an activated cysteinamide;

attaching a mercaptopropionic acid to the 2-7 eptifibatide sequence through a disulfide linkage between the mercaptopropionic acid and the ACys-NH$_2$ of the 2-7 eptifibatide sequence, thereby forming a compound of formula I:

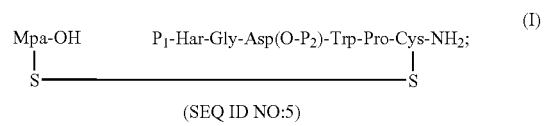

(SEQ ID NO:5)

wherein
Mpa is mercaptopropionic acid;
Cys-NH$_2$ is cysteinamide;

removing $P_1$ from the Har of the compound of formula I, thereby forming a compound of formula II:

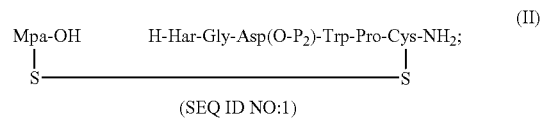

(SEQ ID NO:1)

coupling the Har and Mpa of the compound of formula II, thereby forming a compound of formula III:

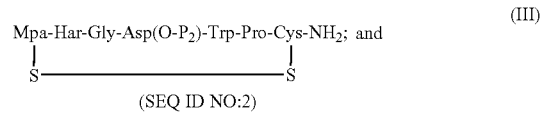

(SEQ ID NO:2)

removing $P_2$ from the Asp residue of the compound of formula III to form eptifibatide.

15. The process of claim 14 wherein $P_2$ is t-butyl.

16. The process of claim 14 wherein $P_1$ is 9-fluorenylmethoxycarbonyl or benzyloxycarbonyl.

17. The process of claim 14 wherein ACys-NH$_2$ is H-Cys(Npys)-NH$_2$.

18. A compound having formula IV:

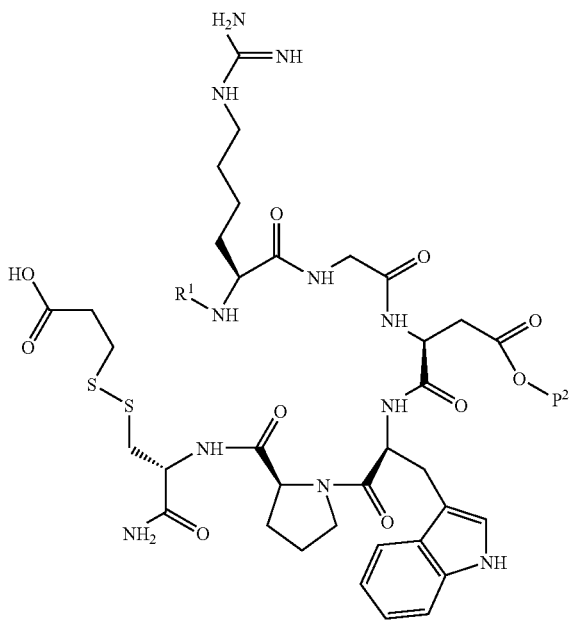

wherein
R₁ is hydrogen or P₁;
P₁ is an amino protecting group; and
P₂ is a carboxyl protecting group.
19. The compound of claim 18 wherein P₂ is t-butyl.
20. The compound of claim 18 wherein R₁ is hydrogen.
21. The compound of claim 20 wherein P₂ is t-butyl.
22. The compound of claim 18 wherein R₁ is P₁.
23. The compound of claim 22 wherein P₁ is 9-fluorenyl-methoxycarbonyl or benzyloxycarbonyl.
24. The compound of claim 23 wherein P₂ is t-butyl.
25. A compound selected from the group consisting of:
Fmoc-Har-Gly-OH;
Fmoc-Har-Gly-O—P₄; and
Fmoc-Har-Gly-Asp(O—P₅)-Trp-Pro-OH (SEQ ID NO:6)

wherein
Fmoc is 9-fluorenyhnethoxycarbonyl;
Har is homoarginine;
Gly is glycine;
Asp is aspartic acid;
Trp is tryptophan;
Pro is proline;
P₄ and P₅ are carboxyl protecting groups.
26. The compound of claim 25 wherein P₄ is pentafluoror-phenol.
27. The compound of claim 25 wherein P₅ is t-butyl.
28. A compound having the following formula:

(SEQ ID NO:13)

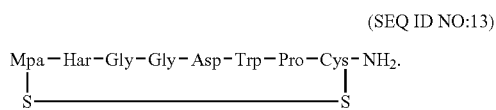

29. A composition comprising eptifibatide and Gly-eptifibatide.
30. The composition of claim 29 comprising at least 99% eptifibatide and Gly-eptifibatide in the range of about 0.01% to about 1%.
31. The composition of claim 30 comprising at least 99% eptifibatide and Gly-eptifibatide in the range of about 0.01% to about 0.1%.
32. The product produced by a process according to claim 4.
33. The product produced by a process according to claim 8.
34. The product produced by a process according to claim 9.
35. The product produced by a process according to claim 11.
36. The product produced by a process according to claim 12.
37. The product produced by a process according to claim 13.

* * * * *

UNITED STATES PATENT AND TRADEMARK OFFICE
CERTIFICATE OF CORRECTION

PATENT NO.        : 7,674,768 B2
APPLICATION NO. : 11/101983
DATED              : March 9, 2010
INVENTOR(S)      : Guojie Ho et al.

It is certified that error appears in the above-identified patent and that said Letters Patent is hereby corrected as shown below:

On the cover page Inventors item (75), please delete "Brice Bonnet, Levallois-Perret (FR)"

On the cover page Inventors item (75), please delete "Christine Devijver, Brussels (BE)"

Column 2, line 45, delete "Formula III:" and replace with -- Formula III and: --

Column 7, line 10, delete "Scheme I" and replace with -- Fig. 1 --

Column 7, line 23, delete "Scheme I" and replace with -- Fig. 1 --

Column 8, line 3, delete "Scheme I" and replace with -- Fig. 1 --

Column 8, line 4, delete "Scheme 2" and replace with -- Fig. 2 --

Column 30, line 48, delete "(SEQ ID NO:1)" and replace with -- (SEQ ID NO:1); --

Column 30, line 58, delete "(SEQ ID NO:2)" and replace with -- (SEQ ID NO:2); --

Column 30, line 60, delete "residue"

Signed and Sealed this

Fourteenth Day of September, 2010

David J. Kappos
*Director of the United States Patent and Trademark Office*

SEQUENCE LISTING

<160> NUMBER OF SEQ ID NOS: 18

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl
<220> FEATURE:
<221> NAME/KEY: MISC_FEATURE
<222> LOCATION: (3)..(3)
<223> OTHER INFORMATION: P2 is a carboxyl protecting group
<220> FEATURE:
<221> NAME/KEY: MISC_FEATURE
<222> LOCATION: (6)..(6)
<223> OTHER INFORMATION: 6,7 disulfide bond
<220> FEATURE:
<221> NAME/KEY: MISC_FEATURE
<222> LOCATION: (7)..(7)
<223> OTHER INFORMATION: Mpa is mercaptopropionic acid

<400> SEQUENCE: 1

Xaa Gly Asp Trp Pro Cys Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Mpa is mercaptopropionic acid
<220> FEATURE:
<221> NAME/KEY: MISC_FEATURE
<222> LOCATION: (1)..(1)
<223> OTHER INFORMATION: 1,7 disulfide bond
<220> FEATURE:
<221> NAME/KEY: MISC_FEATURE
<222> LOCATION: (2)..(2)
<223> OTHER INFORMATION: Har is homoarginyl
<220> FEATURE:
<221> NAME/KEY: MISC_FEATURE
<222> LOCATION: (4)..(4)
<223> OTHER INFORMATION: P2 is a carboxyl protecting group
<220> FEATURE:
<221> NAME/KEY: MISC_FEATURE
<222> LOCATION: (7)..(7)
<223> OTHER INFORMATION: Cys-NH2 is cysteinamide

<400> SEQUENCE: 2

Xaa Xaa Gly Asp Trp Pro Cys
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: P1 is an amino protecting group; Har is
      homoarginyl
<220> FEATURE:

```
<221> NAME/KEY: MISC_FEATURE
<222> LOCATION: (3)..(3)
<223> OTHER INFORMATION: P2 is a carboxyl protecting group

<400> SEQUENCE: 3

Xaa Gly Asp Trp Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: P1 is an amino protecting group; Har is
      homoarginyl
<220> FEATURE:
<221> NAME/KEY: MISC_FEATURE
<222> LOCATION: (3)..(3)
<223> OTHER INFORMATION: P2 is a carboxyl protecting group
<220> FEATURE:
<221> NAME/KEY: MISC_FEATURE
<222> LOCATION: (6)..(6)
<223> OTHER INFORMATION: ACys-NH2 is activated cysteinamide residue

<400> SEQUENCE: 4

Xaa Gly Asp Trp Pro Cys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: P1 is an amino protecting group; Har is
      homoarginyl
<220> FEATURE:
<221> NAME/KEY: MISC_FEATURE
<222> LOCATION: (3)..(3)
<223> OTHER INFORMATION: P2 is a carboxyl protecting group
<220> FEATURE:
<221> NAME/KEY: MISC_FEATURE
<222> LOCATION: (6)..(6)
<223> OTHER INFORMATION: Cys-NH2 is cysteinamide
<220> FEATURE:
<221> NAME/KEY: MISC_FEATURE
<222> LOCATION: (6)..(6)
<223> OTHER INFORMATION: 6,7 disulfide bond
<220> FEATURE:
<221> NAME/KEY: MISC_FEATURE
<222> LOCATION: (7)..(7)
<223> OTHER INFORMATION: Mpa is mercaptopropionic acid

<400> SEQUENCE: 5

Xaa Gly Asp Trp Pro Cys Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
```

```
<223> OTHER INFORMATION: Har is homoarginyl
<220> FEATURE:
<221> NAME/KEY: MISC_FEATURE
<222> LOCATION: (3)..(3)
<223> OTHER INFORMATION: P5 is a carboxyl protecting group

<400> SEQUENCE: 6

Xaa Gly Asp Trp Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Mpa is mercaptopropionic acid
<220> FEATURE:
<221> NAME/KEY: MISC_FEATURE
<222> LOCATION: (1)..(1)
<223> OTHER INFORMATION: 1,7 disulfide bond
<220> FEATURE:
<221> NAME/KEY: MISC_FEATURE
<222> LOCATION: (2)..(2)
<223> OTHER INFORMATION: Har is homoarginyl
<220> FEATURE:
<221> NAME/KEY: MISC_FEATURE
<222> LOCATION: (7)..(7)
<223> OTHER INFORMATION: Cys-NH2 is cysteinamide

<400> SEQUENCE: 7

Xaa Xaa Gly Asp Trp Pro Cys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl

<400> SEQUENCE: 8

Xaa Gly Asp Trp Pro
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl

<400> SEQUENCE: 9

Xaa Gly Asp Trp Pro Cys
1               5

<210> SEQ ID NO 10
<211> LENGTH: 7
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl
<220> FEATURE:
<221> NAME/KEY: MISC_FEATURE
<222> LOCATION: (6)..(6)
<223> OTHER INFORMATION: Cys-NH2 is cysteinamide
<220> FEATURE:
<221> NAME/KEY: MISC_FEATURE
<222> LOCATION: (6)..(6)
<223> OTHER INFORMATION: 6,7 disulfide bond
<220> FEATURE:
<221> NAME/KEY: MISC_FEATURE
<222> LOCATION: (7)..(7)
<223> OTHER INFORMATION: Mpa is mercaptopropionic acid

<400> SEQUENCE: 10

Xaa Gly Asp Trp Pro Cys Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl
<220> FEATURE:
<221> NAME/KEY: MISC_FEATURE
<222> LOCATION: (6)..(6)
<223> OTHER INFORMATION: Cys-NH2 is cysteinamide
<220> FEATURE:
<221> NAME/KEY: MISC_FEATURE
<222> LOCATION: (6)..(6)
<223> OTHER INFORMATION: 6,7 disulfide bond
<220> FEATURE:
<221> NAME/KEY: MISC_FEATURE
<222> LOCATION: (7)..(7)
<223> OTHER INFORMATION: Mpa is mercaptopropionic acid

<400> SEQUENCE: 11

Xaa Gly Asp Trp Pro Cys Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Mpa is mercaptopropionic acid
<220> FEATURE:
<221> NAME/KEY: MISC_FEATURE
<222> LOCATION: (1)..(1)
<223> OTHER INFORMATION: 1,7 disulfide bond
<220> FEATURE:
<221> NAME/KEY: MISC_FEATURE
<222> LOCATION: (2)..(2)
<223> OTHER INFORMATION: Har is homoarginyl
<220> FEATURE:
<221> NAME/KEY: MISC_FEATURE
<222> LOCATION: (7)..(7)
<223> OTHER INFORMATION: Cys-NH2 is cysteinamide

<400> SEQUENCE: 12
```

```
Xaa Xaa Gly Asp Trp Pro Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Mpa is mercaptopropionic acid
<220> FEATURE:
<221> NAME/KEY: MISC_FEATURE
<222> LOCATION: (1)..(1)
<223> OTHER INFORMATION: 1,8 disulfide bond
<220> FEATURE:
<221> NAME/KEY: MISC_FEATURE
<222> LOCATION: (2)..(2)
<223> OTHER INFORMATION: Har is homoarginyl
<220> FEATURE:
<221> NAME/KEY: MISC_FEATURE
<222> LOCATION: (8)..(8)
<223> OTHER INFORMATION: Cys-NH2 is cysteinamide

<400> SEQUENCE: 13

Xaa Xaa Gly Gly Asp Trp Pro Cys
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl

<400> SEQUENCE: 14

Xaa Gly Asp Trp Pro
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl

<400> SEQUENCE: 15

Xaa Gly Asp Trp Pro Asp Trp Pro
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl
<220> FEATURE:
<221> NAME/KEY: MISC_FEATURE
```

```
<222> LOCATION: (6)..(6)
<223> OTHER INFORMATION: Cys(NH2) is cysteinamide
<220> FEATURE:
<221> NAME/KEY: MISC_FEATURE
<222> LOCATION: (7)..(7)
<223> OTHER INFORMATION: Mpa is mercaptopropionic acid

<400> SEQUENCE: 16

Xaa Gly Asp Trp Pro Cys Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl
<220> FEATURE:
<221> NAME/KEY: MISC_FEATURE
<222> LOCATION: (6)..(6)
<223> OTHER INFORMATION: Cys(NH2) is cysteinamide
<220> FEATURE:
<221> NAME/KEY: MISC_FEATURE
<222> LOCATION: (7)..(7)
<223> OTHER INFORMATION: Mpa is mercaptopropionic acid

<400> SEQUENCE: 17

Xaa Gly Asp Trp Pro Cys Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Har is homoarginyl

<400> SEQUENCE: 18

Xaa Gly Asp Trp Pro Cys
1               5
```